(12) United States Patent
Lascombes

(10) Patent No.: US 6,444,174 B1
(45) Date of Patent: Sep. 3, 2002

(54) CARTRIDGE FOR THE PREPARATION OF A SOLUTION FOR MEDICAL USE

(75) Inventor: Jean-Jacques Lascombes, Toulouse (FR)

(73) Assignee: Laboratoire Soludia, Montgiscard (FR)

( * ) Notice: Subject to any disclaimer, the term of this patent is extended or adjusted under 35 U.S.C. 154(b) by 0 days.

(21) Appl. No.: 09/500,095

(22) Filed: Feb. 8, 2000

(51) Int. Cl.[7] ................................................. B01L 3/00
(52) U.S. Cl. ..................... 422/102; 422/99; 206/219; 215/DIG. 8
(58) Field of Search .................. 422/99, 102; 206/219; 215/DIG. 8

(56) References Cited

U.S. PATENT DOCUMENTS

| | | | | |
|---|---|---|---|---|
| 4,865,813 A | * | 9/1989 | Leon | |
| 5,318,750 A | | 6/1994 | Lascombes | |
| 5,431,276 A | * | 7/1995 | Lialin | |
| 5,455,009 A | * | 10/1995 | Vogler et al. | |
| 5,609,827 A | * | 3/1997 | Russel et al. | |
| 5,631,166 A | * | 5/1997 | Jewell | |

* cited by examiner

Primary Examiner—T. Tung
(74) Attorney, Agent, or Firm—Carter & Schnedler

(57) ABSTRACT

The present invention concerns cartridges adapted to provide a solution for medical use such as a dyalysis solution by dissolving a plurality of substances in powder form in at least one liquid.

The cartridge according to the invention comprises a container including a lateral wall, a bottom wall unitary with the lateral wall, the lateral and bottom walls delimiting a main volume, a central nucleus unitary with the bottom wall, the height of the central nucleus being substantially equal to that of the lateral wall to define an annular volume in the main volume, at least two separation walls imperviously unitary with the bottom wall, with the interior surface of the lateral wall and with the exterior surface of the central nucleus to delimit two secondary volumes in the annular volume, and at least two fluid connections adapted to connect the exterior of the container with the two secondary volumes.

21 Claims, 4 Drawing Sheets

CARTRIDGE FOR THE PREPARATION OF A SOLUTION FOR MEDICAL USE

BACKGROUND OF THE INVENTION (a) Field of the Invention

The present invention concerns cartridges capable of providing a solution for medical use by dissolving a plurality of substances in powder form in at least one liquid, and more particularly, cartridges that can be used to provide a dialysis solution.

(b) Description of Prior Art

It is known that, in many fields, for example in the medical field, it is necessary to prepare solutions according to well-specified dosages in order to carry out specific treatments. Such is for example the case of solutions for hemodialysis sessions.

A number of processes and devices have already been perfected to provide such solutions for medical use, for example the one which is described in U.S. Pat. No. 5,318,750, in the name of the Applicant.

The preparation of a solution for medical use by dissolving a plurality of substances in powder form in a carrier fluid, described in this document, is carried out by means of a device in which these substances are contained in cells and which comprises a first duct in communication with an inlet to the cells for introducing the carrier fluid in the cells in order to provide a solute in the cells, a second duct communicating with an outlet from the cells to bring the solutes produced in the cells towards a mixing point located upstream of a place of use, measuring means to measure the concentration of the solutes and a flow control means to modify the concentration of the solutes in response to the information supplied by at least the measuring means, all the substances required for the preparation of the solution being dissolved in the cells and each cell containing at least on of these substances in powder form.

It must also be mentioned that these cells are intended to be used in a hospital environment or the like, where it is absolutely necessary that the number of manipulations, which are required for carrying out the preparation, be restricted to a minimum. The few manipulations that must absolutely be carried out should also be as simple and rapid as possible, so as to facilitate the work of the nursing staff and to reduce as much as possible the time during which the sick person is under treatment.

SUMMARY OF THE INVENTION

Therefore, an aim of the invention is to provide a cartridge for the preparation of a solution for medical use by dissolving a plurality of substances in powder form in at least one liquid, and more particularly cartridges enabling to provide a dialysis solution, which can easily be used by practitioners which must intervene on patients by means of the products contained in these cartridges.

Another aim of the present invention is to provide such a cartridge for medical use, which can be supplied in so-called dry and sterile form, and also be immediately ready to be used by practitioners.

Another aim of the present invention is to provide such a cartridge for medical use which is convenient to handle by practitioners without requiring them to take specific handling cares other than those which are required in the practice of their intervention.

Another aim of the present invention is to provide such a cartridge for medical use that is easy to store while being immediately ready to be used without requiring a specific lengthy and delicate operation.

Another aim of the present invention is to provide such a cartridge for medical use which, altogether, protects particular well the products in powder form awaiting to be used and which can be easily reused after having been refilled.

Another aim of the present invention is to provide such a cartridge for medical use, which can be easily sterilized and encapsulated after or before sterilization.

More specifically, it is an object of the present invention to provide a cartridge enabling to provide a solution for medical use by dissolving a plurality of substances in powder form in at least one liquid and which comprises:

a container comprising a lateral wall of substantially revolving shape defining an opening at one of its two ends, a bottom wall at the other end of said lateral wall, the bottom wall being unitary with the lateral wall, the lateral and bottom walls defining a main volume, a central nucleus of substantially revolving shape provided interiorly of the main volume, said central nucleus being unitary, through one of its two ends, with said bottom wall and having a revolving axis which substantially coincides with that of the lateral wall, said central nucleus having a height substantially equal to that of said lateral wall thereby defining an annular volume in said main volume, at least two separation walls imperviously unitary with the bottom wall, with the inner surface of the lateral wall and with the outer surface of said central nucleus to define at least two secondary volumes in said annular volume, the secondary volumes having predetermined sizes depending on amounts of substances in powder form to be mixed therein with a fluid and capable of forming solutions of the substances in the fluid;

at least two fluid connections mounted in the bottom wall, and adapted to provide connections between the outer part of said container respectively with the two secondary volumes;

wherein the fluid connections are arranged to deliver a fluid to the secondary volumes, the fluid to be mixed with the substances, and to withdraw therefrom the solutions formed therein.

It is also an object of the present invention to provide a cartridge enabling to provide a dialysis solution, and which comprises:

a container comprising a lateral wall of substantially revolving shape defining an opening at one of its two ends, a bottom wall, said bottom wall being unitary with said lateral wall, said lateral and bottom walls defining a main volume, a central nucleus of substantially revolving shape provided interiorly of said main volume, said central nucleus being unitary, through one of its two ends, with said bottom wall and having a revolving axis which substantially coincides with that of the lateral wall, said central nucleus having a height substantially equal to that of said lateral wall thereby defining an annular volume in said main volume, four separation walls imperviously unitary with the bottom wall, with the interior surface of the lateral wall and with the exterior surface of said central nucleus to define four secondary volumes in said annular volume, said secondary volumes having predetermined sizes depending on amounts of substances in powder form that said secondary volumes should contain, said substances in powder form to be mixed therein with a fluid and capable of forming solutions of said substances in said fluid;

at least four fluid connections mounted in said bottom wall, and adapted to provide connections between the exterior of said container respectively with the four secondary volumes; and wherein said fluid connections are arranged to deliver a fluid to said secondary volumes, said fluid to be mixed with said substances in powder form, and to withdraw therefrom said solutions formed therein.

BRIEF DESCRIPTION OF DRAWINGS

Other characteristics and advantages of the present invention will appear from the description which follows of an embodiment of a cartridge according to the invention given with reference to the annexed drawings by way of illustration but without limitation, in which:

FIG. 1 to 5 represent only one embodiment of a cartridge according to the invention and for the purpose of facilitating the understanding of the present description, the same references represent in these figures the same elements, notwithstanding the figure on which these references appear. In the same manner, if elements are not specifically indicated on one of these figures, their references may easily be found by referring to another figure.

Figure 1:
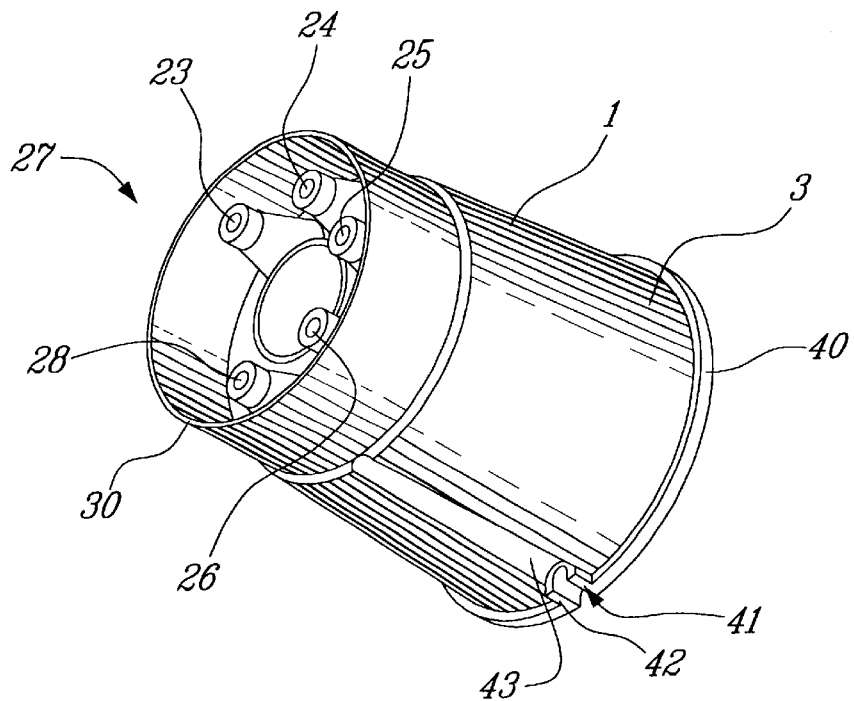
FIGS. 1 and 2 represent this embodiment in two perspective views according to two different angles it being understood that FIG. 2 does not contain the element consisting of a cover.
Figure 2:
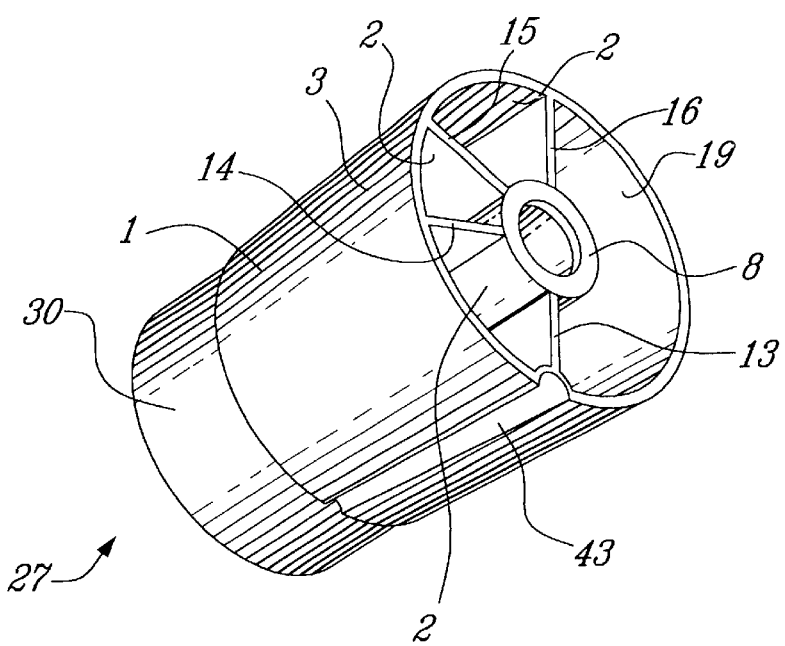

Applicant points out that FIGS. 1 and 2 represent one embodiment of the object of the invention and that there may be other embodiments which correspond to the definition of this invention.

Applicant also points out that according to the definition of the invention, when the object of the invention includes "at least one" element having a given function, the described embodiment may include a plurality of these elements.

Applicant also points out that, if the embodiment of the object of the invention as illustrated includes a plurality of elements with similar function and that, if, in the description, it is not mentioned that the object of this invention must include a specific number of these elements, the object of the invention could be defined as including "at least one" of these elements.

DESCRIPTION OF PREFERRED EMBODIMENT

Subject to what has been mentioned above, the present invention concerns a cartridge for providing a preparation of a solution for medical use by dissolving a plurality of substances in powder form in at least one liquid.

With reference to the drawings, this cartridge comprises a container 1 defining a main volume 2. The container includes a lateral wall 3 of substantially revolving shape defining respectively at one of its ends 7 an opening 5 and a bottom wall 6 which is unitary with the other end 7 of the lateral wall, the lateral and bottom walls defining the main volume 2 mentioned above. The cartridge also comprises a central nucleus 8 of substantially revolving shape, which is unitary, through one of its two ends 9, 10, with bottom wall 6 so that its revolving axis 11 substantially coincides with that of lateral wall 3, the height of the central nucleus being substantially equal to that of the lateral wall to define an annular volume 12 entirely contained within main volume 2, and at least two separation walls 13, 14, 15, 16 imperviously unitary with bottom wall 6, interior surface 17 of the lateral wall 3 and the exterior surface 18 of the central nucleus 8 to define at least two secondary volumes 19–22 in annular volume 12.

The cartridge additionally comprises at least two fluid connection 23–26 mounted to cooperate with bottom wall 6, these two fluid connections enabling to connect the exterior of container 1 respectively with two secondary volumes 19–22. These connections may be of any type, for example of the type as illustrated in the figures, to connect for example a fluid duct thereto, so as to be able to feed the secondary volumes with a fluid and obtain as it will be mentioned later, a dissolution of the product in powder form which is present in the secondary volumes.

Preferably, the cartridge includes a protection crown 30 which is unitary with bottom wall 6 and surrounds fluid connections 23–26, the height of the crown taken from the bottom wall being larger than the height of the fluid connections taken from the same bottom wall. In this manner, the cartridge may rest on a ground surface without any contact of the connections with the ground, thereby imparting to this cartridge a protection which is important for its later use.

Figure 3:
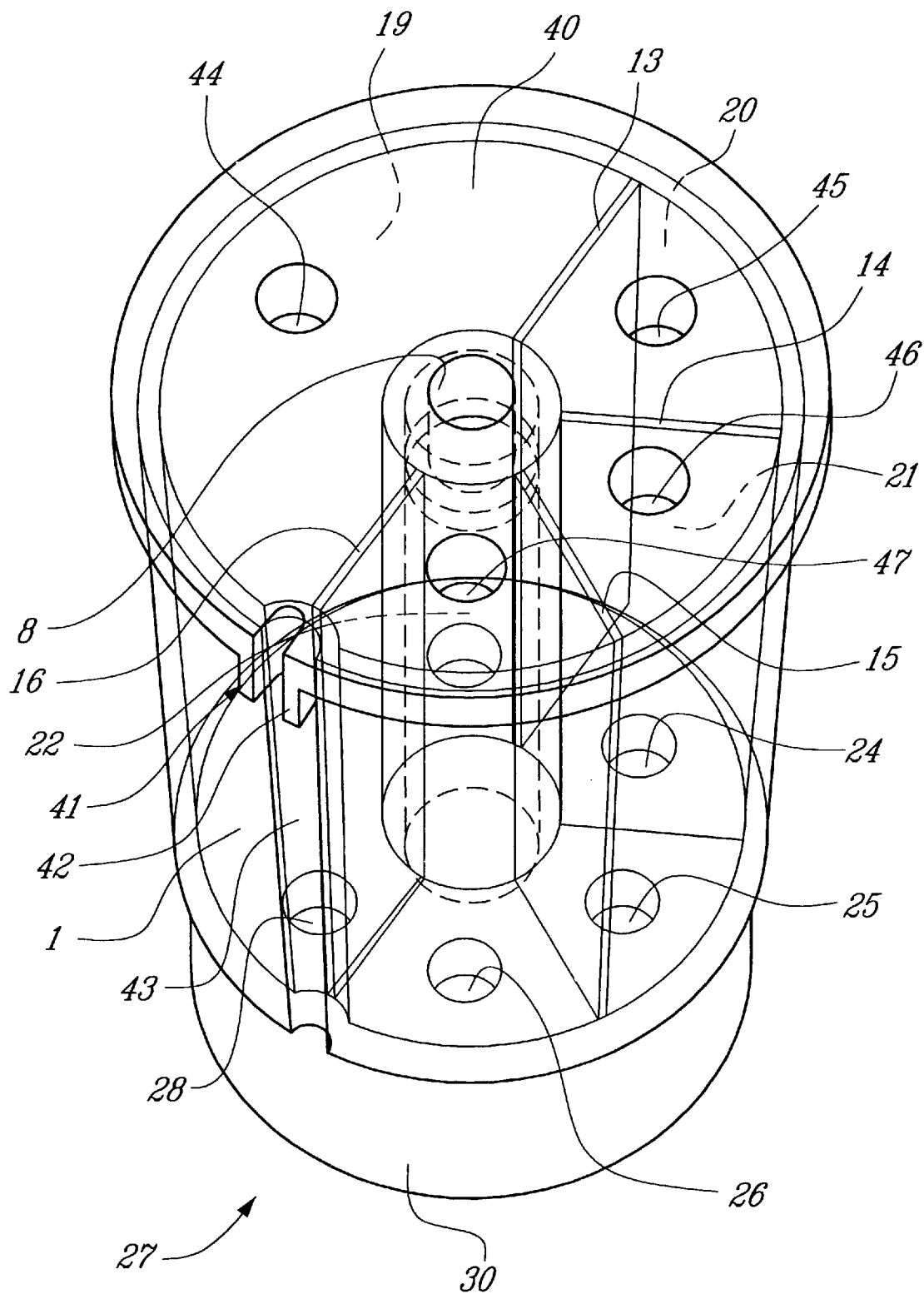
FIG. 3 is a transparent view.
Figure 4:
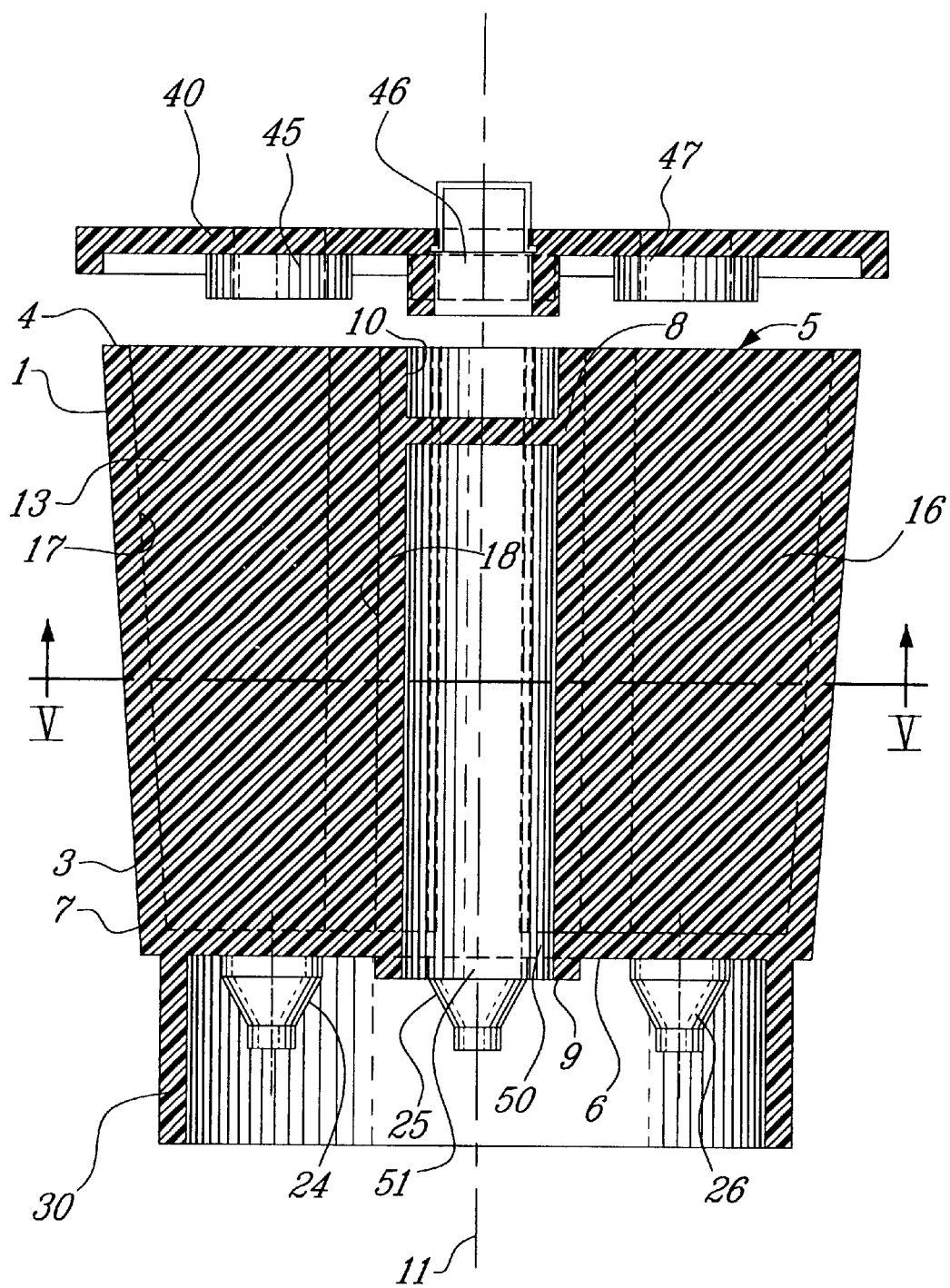
FIG. 4 is a longitudinal cross-section along line IV—IV of FIG. 5.
Figure 5:
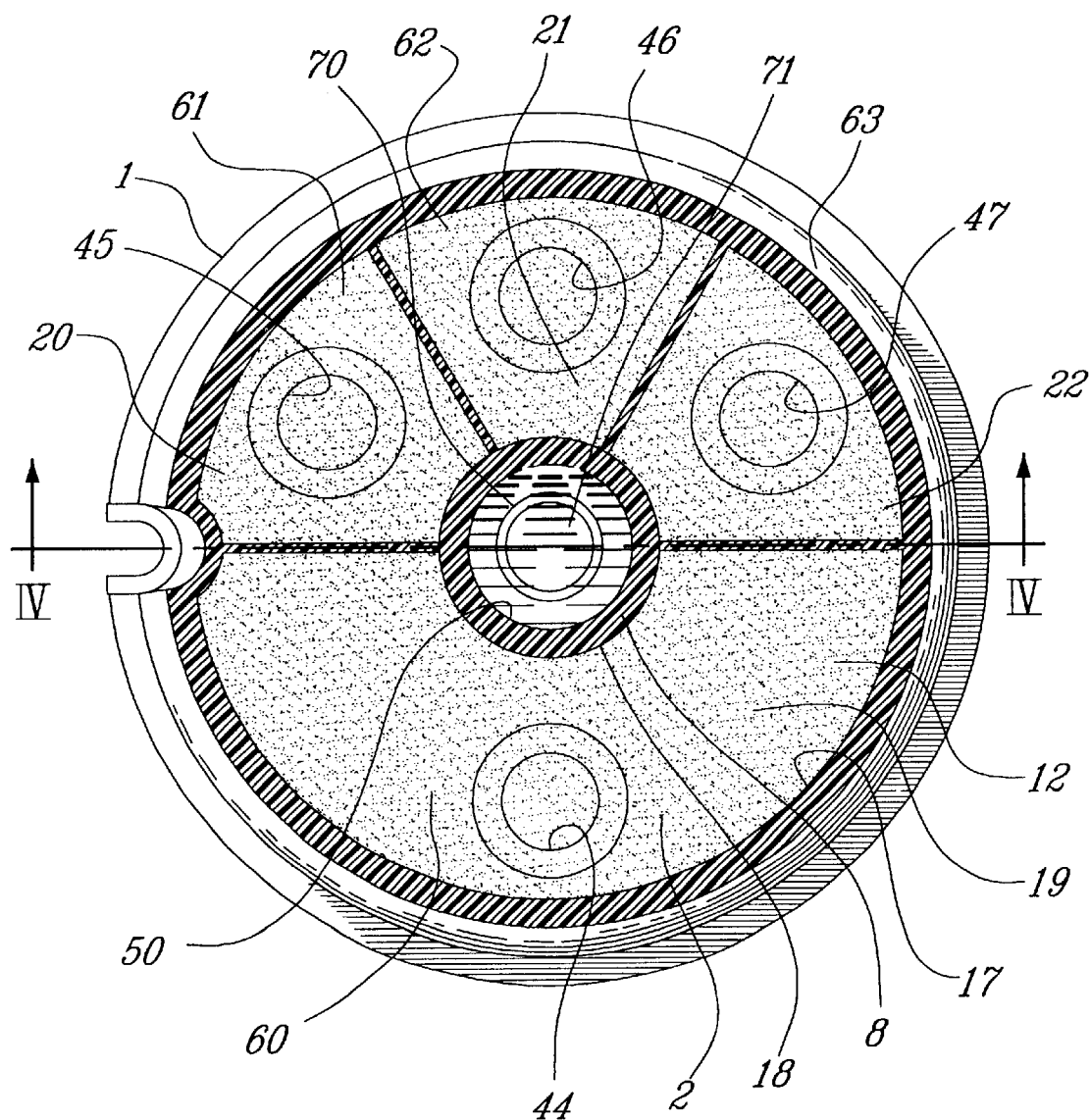
FIG. 5 is a transverse cross-section along line V—V of FIG. 4.

In addition, the cartridge advantageously includes, as better illustrated in FIGS. 1, 3 and 4, a cover 40 capable to close opening 5 of container 1.

Moreover, the cartridge contains means 41 to angularly select the position of cover 40 on opening 5 with respect to lateral wall 3 so that the cover is in a given position with respect to the container. Means 41 may be constituted in different manner, advantageously however they are as illustrated more particularly in FIGS. 1, 2 and 3, and comprise at least one projecting part 42 provided on either the cover or lateral wall, for example, in the illustrated embodiment, on cover 40, and a hollow part 43 which supplements the projecting part, the hollow part being provided on lateral wall 3 in the illustrated embodiment. Of course, the projecting part may also be provided on the lateral wall, and in this case, the hollow part is on the cover.

In this manner, with the angularly selecting means 41, if cover 40 includes at least two orifices 44–47, for example for supplying a powder or the like, the two orifices will be respectively disposed opposite the secondary volumes 19–22 for filling them or completing their filling if necessary.

As mentioned previously, these cartridges are intended to provide solutions for medical use by dissolving a plurality of substances in powder form in at least one liquid, more specifically sterilized water. However, it is sometimes necessary to use another fluid. Therefore it is very interesting that the cartridge be supplied with this specific fluid and that it be transported with the latter present therein at the same time.

In addition, the cartridge advantageously includes a chamber 50 provided in the central nucleus 8 which may directly or indirectly be used as supply for this specific fluid and therefore it is advantageous that this chamber includes an opening 51 formed at the level of the bottom wall.

The cartridge described above is adapted to provide solutions for medical use by dissolving a plurality of substances in powder form in at least one liquid. However, it finds a particularly advantageous application in the preparation of dialysis solutions.

A cartridge for this application is more particularly represented in FIGS. 1 to 5. Also for this application, it includes more particularly four separation walls 13–16 which are imperviously unitary with bottom wall 6, the interior surface 17 of the lateral wall 3 and the exterior surface 18 of the central nucleus 8 to define four secondary volumes 19–22 in annular volume 12. As a result at least four fluid connections 23–26 mounted to cooperate with bottom wall 6, these four fluid connections connecting the exterior 27 of container 1 respectively with the four secondary volumes 19–22.

In this above defined embodiment, the first 19, second 20, third 21 and fourth 22 secondary volumes 19–22 respectively represent 50%, 20%, 10% and 20% of the annular volume 12. In addition, the first secondary volume 19 having a volume representing 50% of the annular volume contains sodium chloride 60, the second 20 and fourth 22 secondary volumes each having a volume equal to 20% of the annular volume respectively contain potassium chloride 61 and calcium chloride 62, and the third secondary volume 21 having a volume equal to 10% of the annular volume contains magnesium chloride 63. These different products were only schematically illustrated in FIG. 5 which is a transversal cross-section of the cartridge, while it is mentioned that the other FIGS. 1 to 4, represent the cartridge of the invention without the products in powder form, so as to simplify these figures and facilitate their understanding.

In a manner perfectly adapted for the realization of a dialysis session, the dimensions of the first, second, third and fourth secondary volumes 19–22 are respectively selected so that the weight of sodium chloride contained in the first secondary volume 19 is 1400 grams, that of potassium chloride contained in the second secondary volume 20 is 67 grams, that of magnesium chloride contained in the third secondary volume 21 is 47 grams and that of calcium chloride contained in the fourth secondary volume 22 is 73 grams. In this manner, it is possible to produce 5 to 6 liters of liquid concentrate which is used during a dialysis session.

To this end, the cartridge comprises an impervious pocket 70 of acetic acid 71, amounting to 200 ml, diluted to 35%, and which is placed in chamber 50.

In this latter embodiment, it is then advantageous that cover 40 includes at least four supply orifices 44–47, these four orifices being respectively disposed opposite the four secondary volumes 19–22 defined above.

However, in an application to dialysis, it should be observed that the first secondary volume 19, has a relatively high value and includes a relatively substantial quantity of product in powder form such as 1400 grams of sodium chloride.

To obtain a more rapid and homogeneous dissolution of this product in a fluid carrier such as water, the cartridge according to the invention preferably includes, as illustrated in the figures of drawings, five fluid connections 23–26 and 28 mounted to cooperate with bottom wall 6.

In these five connections, two 23, 28 connect the exterior of the container with the first secondary volume 19, one of these two connections 23 and 28 respectively constituting an inlet for the dissolution fluid and the outlet of the solution once it is obtained. In return, the other three connections 24–26 connecting the exterior 27 of container 1 respectively with the second 20, third 21 and fourth 22 secondary volumes simultaneously constitute the inlet of the dissolution fluid and the outlet of the solution once it is obtained.

In the above description, the aims of the present invention as specified in the preamble of the present description and others which have been mentioned throughout this description have been reached.

It must additionally be mentioned that the use of a cartridge for example the one which has been described in its application to dialysis will not specifically be described here, since this use can be deducted without difficulty from the description made in the document defining the prior art and referred to in the preamble of the present description, such as U.S. Pat. No. 5,318,750.

I claim:

1. Cartridge for providing a solution for medical use, said solution being obtained by dissolving a plurality of substances in powder form in at least one liquid, said cartridge comprising:

a container including a lateral wall of substantially revolving shape defining an opening at one of its two ends, a bottom wall at the other end of said lateral wall, said bottom wall being unitary with said lateral wall, said lateral and bottom walls defining a main volume, a central nucleus of substantially revolving shape provided interiorly of said main volume, said central nucleus being unitary, through one of its two ends, with said bottom wall and having a revolving axis which substantially coincides with that of the lateral wall, said central nucleus having a height substantially equal to that of said lateral wall thereby defining an annular volume inside said main volume, at least two separation walls imperviously unitary with said bottom wall, with the interior surface of the lateral wall and with the exterior surface of said central nucleus to define at least two secondary volumes in said annular volume, said secondary volumes having predetermined sizes depending on amounts of substances in powder form that said secondary volumes should contain, said substances in powder form to be mixed therein with a fluid and capable of forming solutions of said substances in said fluid;

at least two fluid connections mounted in said bottom wall, and adapted to provide connections between the exterior of said container respectively with the two secondary volumes;

wherein said fluid connections are arranged to deliver a fluid to said secondary volumes, said fluid to be mixed with said substances, and to withdraw therefrom said solutions formed therein.

2. Cartridge according to claim 1, in which a protection crown, which is unitary with said bottom wall, surrounds the two fluid connections, the height of said crown taken from said bottom wall being greater than the height of said fluid connections taken from this same bottom wall.

3. Cartridge according to claim 1, which also comprises a cover capable of covering the opening of the container.

4. Cartridge according to claim 3, and comprising means for angularly selecting the position of the cover on said opening with respect to said lateral wall.

5. Cartridge according to claim 4, in which the means for angularly selecting the position of the cover on said opening are made of at least one projecting part provided on the cover and of a hollow part complementary of said projection part, said hollow part being provided on the lateral wall.

6. Cartridge according to claim 4, in which the means for angularly selecting the position of the cover on said opening are made of at least one projecting part provided on the lateral wall and of at least one hollow part that is complementary with said projection part, said hollow part being provided on the cover.

7. Cartridge according to claim 3, in which said cover includes at least two feeding orifices, these two orifices being respectively disposed opposite the two secondary volumes.

8. Cartridge according to claim 1, in which a chamber adapted to contain a quantity of said fluid is additionally provided in said central nucleus.

9. Cartridge according to claim 8, in which said chamber comprises an opening provided at the level of the bottom wall.

10. Cartridge for providing a dialysis solution, which comprises:

a container including a lateral wall of substantially revolving shape defining an opening at one of its two ends, a bottom wall of the other end of said lateral wall, said bottom wall being unitary with said lateral wall, said lateral and bottom walls defining a main volume, a central nucleus of substantially revolving shape provided interiorly of said main volume, said central nucleus being unitary, through one of its two ends, with said bottom wall and having a revolving axis which substantially coincides with that of the lateral wall, said central nucleus having a height substantially equal to that of said lateral wall thereby defining an annular volume in said main volume, four separation walls imperviously unitary with the bottom wall, with the interior surface of the lateral wall and with the exterior surface of said central nucleus to define four secondary volumes in said annular volume, said secondary volumes having predetermined sizes depending on amounts of substances in powder form that said secondary volumes should contain, said substances in powder form to be mixed therein with a fluid and capable of forming solutions of said substances in said fluid;

at least four fluid connections mounted in said bottom wall, and adapted to provide connections between the exterior of said container respectively with the four secondary volumes; and wherein said fluid connections are arranged to deliver a fluid to said secondary volumes, said fluid to be mixed with said substances in powder form, and to withdraw therefrom said solutions formed therein.

11. Cartridge according to claim 10, in which the first, second, third and fourth secondary volumes respectively represent 50%, 20%, 10% and 20% of the annular volume.

12. Cartridge according to claim 11, in which the first secondary volume having a volume representing 50% of the annular volume contains sodium chloride, the second and fourth secondary volumes, each having a volume which is equal to 20% of the annular volume, respectively contain potassium chloride and calcium chloride, and the third secondary volume having a volume equal to 10% of the annular volume contains magnesium chloride.

13. Cartridge according to claim 12, in which the dimensions of the first, second, third and fourth secondary volumes are respectively determined so that the weight of sodium chloride present in the first secondary volume is 1400 grams, the weight of potassium chloride present in the second secondary volume is 67 grams, the weight of magnesium chloride present in the third secondary volume is 47 grams and the weight of calcium chloride resent in the fourth secondary volume is 73 grams.

14. Cartridge according to claim 11, in which five fluid connections are mounted to cooperate with the bottom wall, two of these five connections adpated to provide connections between the exterior of the container with the first secondary volume, these two connections respectively defining a fluid inlet and a fluid outlet, the three other connections providing communication respectively between the exterior of the container and the second, third and fourth secondary volumes, each of these three connections simultaneously defining a fluid inlet and a fluid outlet.

15. Cartridge according to claim 10, in which a chamber is additionally provided in said central nucleus and a bag of acetic acid is disposed in said chamber.

16. Cartridge according to claim 10, in which a protection crown which is unitary with the bottom wall, surrounds the four fluid connections, the height of said crown taken from the bottom wall being greater than the height of the fluid connections taken from this same bottom wall.

17. Cartridge according to claim 10, which also comprises a cover capable of covering the opening of the container.

18. Cartridge according to claim 17, and which comprises means for angularly selecting the position of the cover on said opening with respect to said lateral wall.

19. Cartridge according to claim 18, in which the means for angularly selecting the position of the cover on said opening are made of at least one projection part provided on the cover and of a hollow part which is complementary of the projection part, said hollow part being provided on the lateral wall.

20. Cartridge according to claim 18, in which the means for angularly selecting the position of the cover on said opening are made of at least one projecting part provided on the lateral wall and of at least one hollow part that is complementary with said projection part, said hollow part being provided on the cover.

21. Cartridge according to claim 17, in which said cover comprises at least four feeding orifices, the four orifices being respectively disposed opposite the four secondary volumes.

* * * * *